United States Patent [19]

Young et al.

[11] Patent Number: 4,724,216
[45] Date of Patent: Feb. 9, 1988

[54] METHOD FOR MEASURING CALCIUM

[75] Inventors: Chung C. Young, Natick; Linda M. Mulholland, Stoughton, both of Mass.

[73] Assignee: Nova Biomedical Corporation, Waltham, Mass.

[21] Appl. No.: 796,194

[22] Filed: Nov. 8, 1985

Related U.S. Application Data

[60] Division of Ser. No. 649,544, Sep. 11, 1984, abandoned, which is a continuation-in-part of Ser. No. 614,251, May 25, 1984, abandoned.

[51] Int. Cl.$^4$ .................................................. G01N 33/20
[52] U.S. Cl. ......................................... 436/79; 204/1 T; 210/698; 436/17; 436/74; 436/177
[58] Field of Search .............. 436/16, 17, 18, 63, 436/74, 79, 150, 163, 174, 177; 204/1 T, 416, 417, 418, 419; 252/408.1; 210/698

[56] References Cited

U.S. PATENT DOCUMENTS

| | | | |
|---|---|---|---|
| 3,934,977 | 1/1976 | Cleaver | 436/79 X |
| 3,996,268 | 12/1976 | Carpenter et al. | 260/544 YX |
| 4,054,488 | 10/1977 | Marbach | 436/18 X |
| 4,222,991 | 9/1980 | Hass | 423/235 |
| 4,314,895 | 2/1982 | Spaziani et al. | 204/418 X |
| 4,363,633 | 12/1982 | Christiansen | 436/16 X |

FOREIGN PATENT DOCUMENTS 0113367 7/1982 Japan ........................................ 436/74

OTHER PUBLICATIONS

Loken et al, J. Bio. Chem., vol. 235, No. 12, pp. 3654–3658, 1960.
Anker et al, Anal. Chem., vol. 53, No. 13, pp. 1970–1974, 1981.
Moore, J., Clin. Invest., vol. 49, pp. 318–334, 1970.
Osswald et al, Clin. Chem., vol. 25, No. 1, pp. 39–43, 1979.

*Primary Examiner*—Barry S. Richman
*Assistant Examiner*—Robert J. Hill, Jr.

[57] ABSTRACT

A releasing reagent for releasing, as ionized calcium, protein-bound calcium in a biological sample for measurement of the ionized calcium, together with any ionized calcium originally present in the sample, using a calcium ion specific electrode, the releasing reagent including monochlorocoacetate salt, formate salt, and formic acid, in concentrations sufficient to render the pH of the sample, when mixed with the reagent, in the range of 4.0 to 5.5. Also disclosed is a method of measuring calcium in a liquid sample using such a releasing reagent.

15 Claims, 1 Drawing Figure

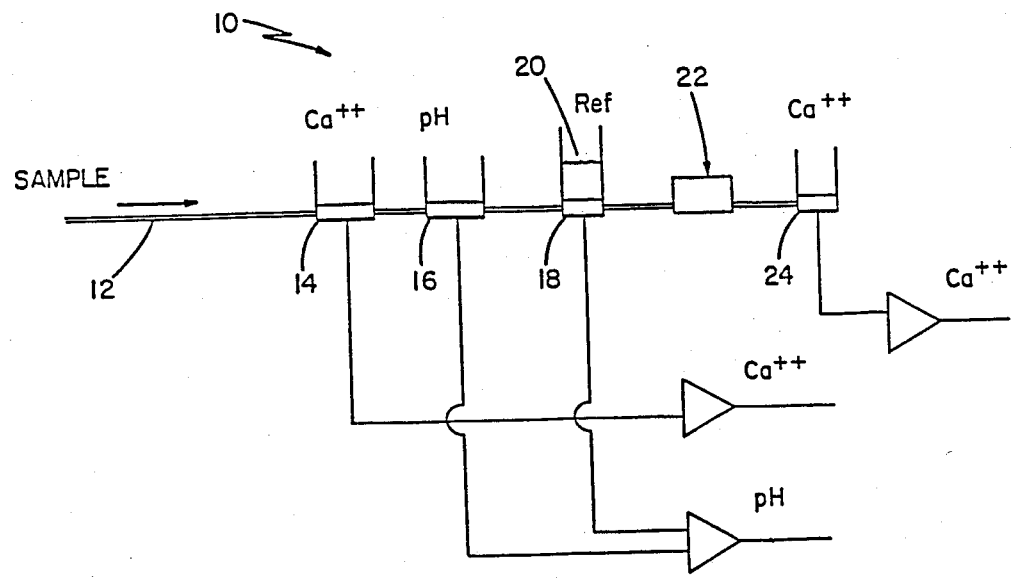

METHOD FOR MEASURING CALCIUM

This application is a division of U.S. Ser. No. 649,544, filed Sept. 11, 1984, now abandoned, which in turn is a continuation-in-part of U.S. Ser. No. 614,251, filed May 25, 1984, now abandoned.

BACKGROUND OF THE INVENTION

This invention relates to the measurement of calcium using ion specific electrodes.

In biological fluids calcium ordinarily exists both in the form of calcium ions ($Ca^{++}$), and calcium complexed with protein and, to a lesser extent, other complexing agents in the fluids. Ion selective calcium electrodes measure only ionized, and not complexed calcium, despite the fact that it would be desirable in some situations to measure, in addition to ionized calcium, "total" calcium, i.e., the sum of ionized and complexed calcium.

It is known that complexed calcium can be released by lowering the pH of the sample containing the complexed calcium. The most efficient releasing of calcium (over 90% calcium released) is observed when a sufficient amount of a strong acid is added to the liquid to lower the pH below 3.0. Such a drastic lowering of pH, however, is inconsistent with optimal operation of conventional calcium electrodes.

In general, the present invention features a releasing reagent for releasing, as ionized calcium, complexed calcium in a liquid sample for measurement of such ionized calcium, together with any ionized calcium originally present in the sample, using a calcium ion specific electrode. The releasing reagent includes formic acid and formate salt (e.g., the sodium salt), in concentrations sufficient to render the pH to the sample, when mixed with the reagent, in the range of 4.0 to 5.5, most preferably 4.5.

The formic acid and formate salt together cause the release of calcium in biological samples. For samples, e.g., spinal fluid, in which complexed calcium is bound not to protein but to other constituents of the liquid, the releasing reagent need not contain ingredients in addition to formic acid and formate salt. For other samples, e.g., serum, which do contain appreciable amounts of protein, it is desirable that the releasing reagent contain an additional component which inhibits precipitation of the protein in the sample. Preferably, this precipitation inhibiting component is the salt of a strong organic acid, e.g., a haloacetate salt such as a monochloroacetate or trifluoroacetate salt. Of these latter two, trifluoroacetate salt is most preferred because of its superior long-term stability.

In particular embodiments of the invention, the concentration of formic acid is between 0.105 Molar and 0.195 Molar, and is preferably about 0.15 Molar; and the concentration of formate salt is between 0.21 Molar and 0.39 Molar, and is preferably about 0.30 Molar.

When the releasing reagent contains monochloroacetate salt, this component is preferably present in a concentration of between 0.385 Molar and 0.715 Molar, most preferably about 0.55 Molar. When trifluoroacetate is present, it is preferably at a concentration of between 0.225 Molar and 0.416 Molar, most preferably about 0.32 Molar.

In other particular embodiments the reagent is for use in an apparatus in which the reagent is added to the sample at the same time as a reference solution is added to the sample; in this instance the reagent includes the reference solution, which is preferably ammonium chloride, preferably present in a concentration of between 1.5 Molar and 3.0 Molar, most preferably 2.0 Molar.

The releasing reagent of the invention provides efficient (greater than 99%) release of complexed calcium while avoiding detrimental extreme acidic conditions. Furthermore, the reagent, including or not including a reference solution, minimizes liquid junction and interference effects.

BRIEF DESCRIPTION OF THE DRAWING

Other objects, features and advantages of this invention will be apparent to those skilled in the art from the following detailed description of a preferred embodiment thereof, taken together with the accompanying drawing, in which:

The FIGURE is a schematic representation of electrode apparatus employing the releasing reagent of the invention. Much of the structure and operation of the apparatus is as described in U.S. Pat. No. 4,314,895, hereby incorporated by reference.

Referring to the Figure, in the preferred embodiment of the present invention the releasing reagent entering the system via line 20 has one of the following two compositions:

2.0 Molar ammonium chloride
0.55 Molar monochloroacetate (sodium salt)
0.15 Molar formic acid
0.30 Molar formate (sodium salt)    (1) or
2.0 Molar ammonium chloride
0.32 Molar trifluoroacetate (sodium salt)
0.15 Molar formic acid
0.30 Molar formate (sodium salt)    (2)

A sample (e.g. urine, blood, or spinal fluid) enters the electrode apparatus via line 12 and flows past conventional calcium ion specific electrode 14 and conventional pH electrode 16, both of which measure their respective ions with reference to conventional reference electrode 18. As the sample flows past reference electrode 18, the releasing reagent of the invention is injected into the system via line 20 and mixes with the sample in mixer 22.

The reagent causes the release of the complexed calcium in the sample so that the released calcium ions, together with calcium ions originally present in the sample, can be measured by the second calcium ion specific electrode 24 (which also uses reference electrode 18) to give a measurement of total calcium.

The illustrated system measures pH, ionized calcium, and total calcium, while maintaining the pH of the sample and reagent mixture at about 4.5. Despite the fairly high, system-compatible pH, calcium releasing is generally close to 100%, providing a relatively accurate total calcium measurement. Since the system also measures originally ionized calcium, complexed calcium can be estimated by subtracting ionized from total calcium.

Other embodiments of the invention are within the following claims. For example, the concentrations of the reagent components can vary within the ranges given above. The pH of the reagent, prior to being mixed with the sample, is not much affected by variations within the stated ranges, and is generally about 4.0 for all formulations. However, the concentration of reagent components, particularly of the formic acid, does affect the pH of the reagent/sample mixture; a greater concentration of acid will produce a mixture with a lower pH. The pH of the mixture, as mentioned above, can range from about 4.0 to 5.5; pH values outside this range at the high end will have inadequate calcium releasing power, while values outside the range at the low end can be harmful to electrode operation.

The concentration of ammonium chloride also has an effect on the operation of the system. Although the main function of ammonium chloride is as a reference solution for the reference electrode, ammonium chloride also aids, to a minor extent, the releasing of complexed calcium. Ammonium chloride concentrations outside the stated range at the high end of the range have the potential of causing interference, while concentrations outside the range at the low end can, in a flow-through system such as that illustrated in the Figure, cause undesirable liquid junction effects.

As mentioned above, the reagent of the invention can be used in systems other than that illustrated in the Figure. For example, the reagent can be used in a system in which a sample stream is split into two streams, one of which flows through a calcium ion specific electrode for measurement of ionized calcium, and the other of which is mixed with the reagent and then flows through a calcium ion specific electrode for measurement of total calcium. In this type of system, a reference solution such as ammonium chloride is not a necessary reagent component, although it can still be used to aid in calcium releasing.

What is claimed is:

1. A method of measuring calcium in a liquid sample comprising releasing, as ionized calcium, bound calcium in said liquid sample by contacting said liquid sample with a releasing reagent comprising formate salt and formic acid, in an amount sufficient to render the pH of said sample, when mixed with said releasing reagent, in the range of 4.0 to 5.5, and then measuring ionized calcium in said sample.

2. The method of claim 1 wherein the formic acid is present in the releasing reagent in a concentration of between 0.105 Molar and 0.195 Molar and the formate salt is present in the releasing reagent in a concentration of between 0.21 Molar and 0.39 Molar.

3. The method of claim 1 wherein said sample contains protein and said releasing reagent further comprises a component capable of inhibiting precipitation of said protein in said sample.

4. The method of claim 3 wherein said precipitation inhibiting component comprises a salt of a strong organic acid.

5. The method of claim 4 wherein said salt of a strong organic acid comprises an acetate salt.

6. The method of claim 5 wherein said acetate salt comprises monochloroacetate salt.

7. The method of claim 6 wherein said monochloroacetate salt is present in the releasing reagent in a concentration between 0.385 Molar and 0.715 Molar.

8. The method of claim 5 wherein said acetate salt comprises trifluoroacetate salt.

9. The method of claim 8 wherein said trifluoroacetate salt is present in the releasing reagent in a concentration between 0.225 Molar and 0.416 Molar.

10. The method of claim 1 wherein said reagent is added to said sample at the same time a reference solution is added to said sample, said releasing reagent further comprising said reference solution.

11. The method of claim 10 wherein said reference solution comprises ammonium chloride.

12. The method of claim 11 wherein said ammonium chloride is present in the releasing reagent in a concentration of between 1.5 molar and 3.0 Molar.

13. The method of claim 12 wherein said formic acid is present in the releasing reagent in a concentration of about 0.15 Molar, said formate salt is present in the releasing reagent in a concentration of about 0.30 Molar, and said ammonium chloride is present in the releasing reagent in a concentration of about 2.0 Molar.

14. The method of claim 13 wherein said releasing reagent further comprises monochloroacetate in a concentration of about 0.55 Molar.

15. The method of claim 13 wherein said releasing reagent further comprises trifluoroacetate in a concentration of about 0.32 Molar.

* * * * *